United States Patent [19]

Schulte-Elte et al.

[11] Patent Number: 4,711,875

[45] Date of Patent: Dec. 8, 1987

[54] COMPOSITION ESSENTIALLY CONSISTING OF TRANS-1-(2,6,6-TRIMETHYLCYCLOHEXYL)-HEXAN-3-OL

[75] Inventors: Karl-Heinrich Schulte-Elte, Onex; Günther Ohloff, Bernex; Bernard L. Müller, Geneva; Wolfgang K. Giersch, Bernex, all of Switzerland

[73] Assignee: Firmenich SA, Geneva, Switzerland

[21] Appl. No.: 788,314

[22] Filed: Oct. 17, 1985

Related U.S. Application Data

[62] Division of Ser. No. 584,501, Feb. 28, 1984, Pat. No. 4,623,750.

[30] Foreign Application Priority Data

Mar. 9, 1983 [CH] Switzerland ............... 1259/83

[51] Int. Cl.$^4$ ............... A61K 7/46; C07C 35/08
[52] U.S. Cl. ............... 512/1; 512/22; 568/832; 568/833; 568/834
[58] Field of Search ............... 252/522 R; 568/832, 568/833, 824, 825, 826, 378

[56] References Cited

U.S. PATENT DOCUMENTS

| 3,928,645 | 12/1975 | Mookherjei et al. | 568/378 |
|---|---|---|---|
| 4,147,886 | 4/1979 | Wiederker | 568/824 |
| 4,169,109 | 9/1979 | Yoshida et al. | 568/378 |
| 4,252,986 | 2/1981 | Klein | 252/522 R |
| 4,311,860 | 1/1982 | Krasnobajew | 568/378 |
| 4,313,855 | 2/1982 | Klein et al. | 252/522 R |
| 4,588,849 | 5/1986 | Schulte-Elte et al. | 568/834 |
| 4,623,750 | 11/1986 | Schulte-Elte et al. | 568/822 |

FOREIGN PATENT DOCUMENTS

| 0118817 | 9/1984 | European Pat. Off. | |
| 2455761 | 6/1976 | Fed. Rep. of Germany. | |
| 3233175 | 3/1983 | Fed. Rep. of Germany | 568/378 |
| 2418214 | 9/1979 | France. | |
| 0739055 | 6/1980 | U.S.S.R. | 568/378 |

OTHER PUBLICATIONS

Schulte-Elte, "Chemical Abstracts", vol. 102 (1985) 79179w.

von B. Prelog, H. Frick, "Uber Die Beiden Diastereomeren Tetrahydro-jonane," Helv. Chim. Acta. vol. XXXI, Fasc. II (1948), pp. 417–422 at pp. 419–421.

*Primary Examiner*—Werren B. Lone
*Attorney, Agent, or Firm*—Pennie & Edmonds

[57] ABSTRACT

Composition consisting of from less than 100% to more than about 80% of trans-1-(2,6,6-trimethylcyclohexyl)-hexan-3-ol and a definite amount, but not more than about 20%, of cis-1-(2,6,6-trimethylcyclohexyl)-hexan-3-ol.

Process for preparing same from β-cyclocitral via a three-, optionally, four-step pathway.

Utilization of the said composition as effective perfume ingredient.

12 Claims, No Drawings

COMPOSITION ESSENTIALLY CONSISTING OF TRANS-1-(2,6,6-TRIMETHYLCYCLOHEXYL)-HEXAN-3-OL

This is a divisional application of U.S. Ser. No. 584,501, now U.S. Pat. No. 4,623,750.

BRIEF SUMMARY OF THE INVENTION

The instant invention relates to a composition of from less than 100% to more than about 80% of trans-1-(2,6,6-trimethylcyclohexyl)-hexan-3-ol and a definite amount, but not more than about 20% of cis-1-(2,6,6-trimethylcyclohexyl)-hexan-3-ol.

The invention relates further to essentially pure trans-1-(2,6,6-trimethylcyclohexyl)-hexan-3-ol.

The invention also provides a perfume composition comprising an odorous effective amount of the above said composition, as well as perfumed articles comprising the same.

An object of the invention is to provide a process for the preparation of the said composition, which process comprises the following sequential steps:

a. the reduction of β-cyclocitral by catalytic hydrogenation to give 1-formyl-2,6,6-trimethyl-cyclohexane, b. the addition of 2-pentanone to the obtained product in the presence of a strong base to give a mixture containing a predominant amount, but not less than about 95% by weight, of trans-1-(2,6,6-trimethylcyclohexyl)-hex-1-en-3-one and a definite amount, but not more than about 5% by weight, of cis-1-(2,6,6-trimethylcyclohexyl)-hex-1-en-3-one, c. the reduction of the mixture thus obtained by a hydrogenation at a pressure higher than the atmospheric pressure and in the presence of catalytic amounts of Raney-nickel, with or without copper chromite, and, optionally, d. the separation of the obtained mixture by means of preparative vapor phase chromatography to give essentially pure trans-1-(2,6,6-trimethylcyclohexyl)-hexan-3-ol.

Finally, this invention relates to novel compositions of matter constituted by intermediate cycloaliphatic ketones and alcohols of formulae

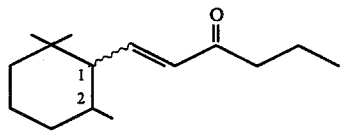

(II)

and

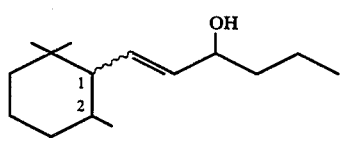

(III)

wherein the wavy line stands for a C—C bond of cis or trans configuration with respect to the methyl group in position 2 of the ring.

BACKGROUND OF THE INVENTION

The prior art describes that 1-(2,6,6-trimethylcyclohexyl)-hexan-3-ol, also known under the name of ethyl-tetrahydroionol, possesses useful odorous properties, namely as a fixative [see DE-AS No. 28 07 584]. By trying to reproduce the process disclosed in said document however, we discovered that the product obtained was in fact constituted by a mixture eminently consisting of cis-1-(2,6,6-trimethylcyclohexyl)-hexan-3-ol accompanied by a minor amount, of the order of about 10 to 12%, of the trans isomer.

The prior art process is illustrated by the following reaction pathway:

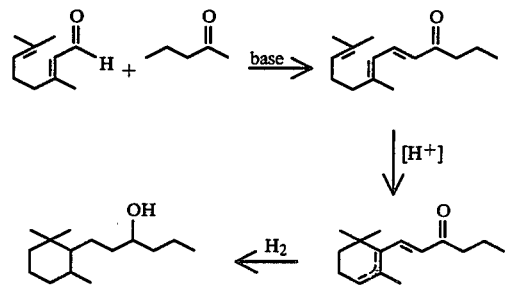

DE-AS No. 28 07 584 is mute however as to the isomeric nature of the product obtained by said process. By way of consequence, it fails to recognize any distinctive character of the odor shown by the individual discreet isomers.

We have discovered surprisingly that trans-1-(2,6,6-trimethylcyclohexyl)-hexan-3-ol not only is a useful perfuming ingredient in its own right, but that its properties are distinct from those of the cis isomer and its power far superior to that shown by this latter compound. For simplicity's sake, the product described in DE-AS No. 28 07 584 will be referred to in the following description by its commercial name, TIMBEROL (origin: Dragoco, Holzminden, FRG).

Thanks to the process of the instant invention, it is now possible to prepare a product eminently consisting of trans-1-(2,6,6-trimethylcyclohexyl)-hexan-3-ol or of a composition consisting of from less than 100% to more than about 80% of trans-1-(2,6,6-trimethylcyclohexyl)-hexan-3-ol and a definite amount, but not more than about 20% of cis-1-(2,6,6-trimethylcyclohexyl)-hexan-3-ol. The difference observed between the odor of these two isomers underlines once again the unpredictability of the phenomenon of odor perception. In effect, though both these compounds develop a scent of woody and ambery type, the trans isomer, and the mixtures thereof containing major amount of it, show a more pronounced animal and ambery character. Its animal note can be defined as being almost faecal. The composition of the invention shows moreover a woody character reminiscent of vetyver oil, whereas TIMBEROL develops a woodiness related to cedar wood or patchouli essential oil.

The difference between the two compounds is even more pronounced with respect to their odor strength. We have discovered that the composition of the invention is remarkably more powerful than TIMBEROL. Evaluated on a paper sniffing strip, it could be established that an alcoholic solution at 5% (by weight in 95% ethanol) of the composition of the invention possesses an odor strength similar to that shown by pure TIMBEROL: its power is therefore about twenty times higher than that of the known commercial compound.

The evaluations of the odor threshold values we have carried out on aqueous solutions, according to Guadagni et al. [J. Amer. Food Agric. 14, 761 (1963)], have indicated a value of 32 ppb (parts per billion) for trans-1-

(2,6,6-trimethylcyclohexyl)-hexan-3-ol and 240 ppb for its cis isomer. The chemical purity of the tested compounds was ≧99% and ≧99.5%, respectively.

Concerning the substantivity of these compounds on textile materials, we could observe that both the composition of the invention and the prior art compound possess an excellent substantivity on fabrics subjected to washing and treatment with liquid and solid detergents, and with fabric softeners of various nature, irrespective of whether they were anionic, cationic or non ionic. However, the degree of substantivity of trans-1-(2,6,6-trimethylcyclohexyl)-hexan-3-ol is higher than that of its cis isomer.

Owing to its properties, trans-1-(2,6,6-trimethylcyclohexyl)-hexan-3-ol and mixtures thereof containing major amount of it possess clear advantages over the prior art compound and consequently their utilization in perfume compositions and perfumed products favorably enlarges the degree of perfumer's creativity.

PREFERRED EMBODIMENTS OF THE INVENTION

According to the invention, trans-1-(2,6,6-trimethylcyclohexyl)-hexan-3-ol is prepared from β-cyclocitral by a three- or four-step process. Said process comprises:

a. the reduction of β-cyclocitral by catalytic hydrogenation to give 1-formyl-2,6,6-trimethyl-cyclohexane, b. the addition of 2-pentanone to the obtained product in the presence of a strong base to give a mixture containing a predominant amount, but not less than about 95% by weight, of trans-1-(2,6,6-trimethylcyclohexyl)-hex-1-en-3-one and a definite amount, but not more than about 5% by weight, of cis-1-(2,6,6-trimethylcyclohexyl)-hex-1-en-3-one, c. the reduction of the mixture thus obtained by a hydrogenation at a pressure higher than the atmospheric pressure and in the presence of catalytic amounts of Raney-nickel, with or without copper chromite, and, optionally, d. the separation of the obtained mixture by means of preparative vapor phase chromatography to give essentially pure trans-1-(2,6,6-trimethylcyclohexyl)-hexan-3-ol.

The above described process of the invention is illustrated by the following reaction pathway:

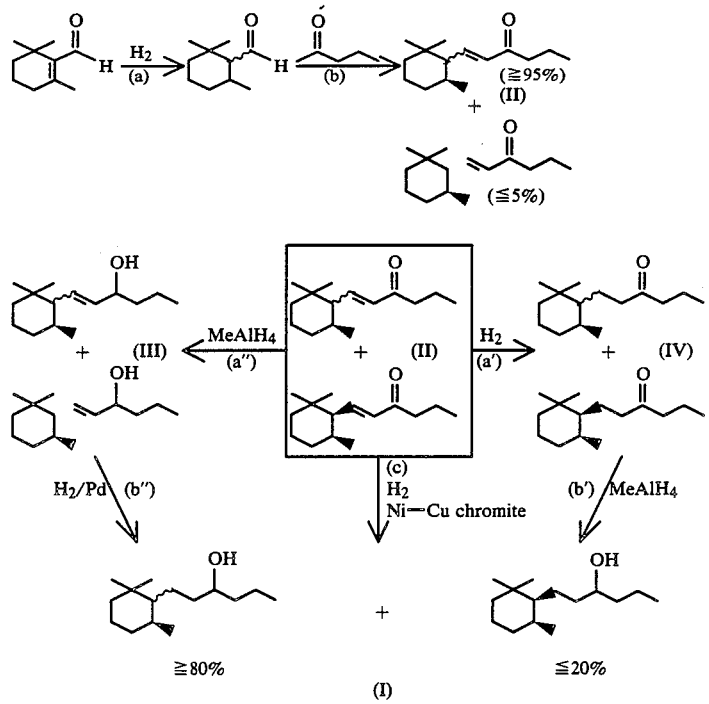

Me=alkali metal

Step a. of the above process is effected according to the method described by V. Prelog et al. [Helv. Chim. Acta, 31, 417 (1948)]. The following step which consists in the addition of 2-pentanone on the obtained dihydrocyclocitral represents an example of aldol condensation whose nature is analogous to that described by Prelog himself [op. cit.] for the addition of acetone. It can be effected in the presence of strong bases of various nature, both organic and mineral. Thus, nitrogen bases, alkali metal alkoxides or hydroxides can be conveniently used. Sodium and potassium alkoxides are preferred. We could determine that the best yields of this step were achieved by using about two equivalents of alkoxide for one equivalent of the starting material. Lower rates of conversion were observed whenever smaller proportions of base had been used. Step c., which consists in the reduction of the ketone of formula

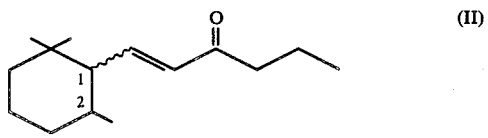

wherein the wavy line stands for a C—C bond of cis- or trans configuration with respect to the methyl group in position 2 of the ring, by means of a catalytic hydrogenation, can be carried out according to a method analogous to that described for the reduction of methylionones to tetrahydromethylionones [see DE-OS No. 24 55 761]. Thus, the hydrogenation can be carried out at a temperature of between about 120° and 200° C., preferably of about 140° C., and at a pressure of 20 to 100 atmospheres. Suitable catalysts include Raney-nickel or mixture of it with copper chromite. It has been observed that at pressure lower than about 50 atm, the presence of copper chromite is not critical, whereas at pressure higher than the said value, copper chromite exerted an influence on the isomers ratio by favoring the formation of the trans isomer. The yields observed of the end product were excellent. There is thus obtained a 1-(2,6,6-trimethylcyclohexyl)-hexan-3-ol whose isomeric configuration corresponds roughly to that of the starting ketone. This implies that whenever a mixture of cis- and trans-1-(2,6,6-trimethylcyclohexyl)-hex-1-en-3-one of definite isomeric content is used as starting material, there is obtained a mixture of cis- and trans-1-(2,6,6-trimethylcyclohexyl)-hexan-3-ol of almost equivalent isomeric ratio.

The above illustrated scheme of the process of the invention shows, in addition to steps a.–c., two variants for the preparation of the invention compositions.

One of them consists in:

(a') the catalytic hydrogenation of ketone (II) to give a compound of formula

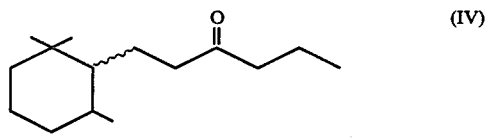

(IV)

and (b') the reduction by means of an alkali metal aluminohydride or alkoxide of compound (IV to give the desired compounds (I).

The other variant consists in:

(a") the reduction of ketone (II) by means of an alkali metal aluminohydride to give a compound of formula

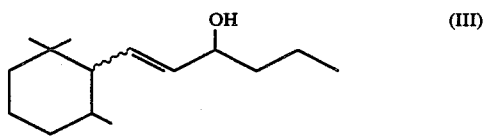

(III)

and (b") the catalytic hydrogenation of compound (III) to give the desired compound (I).

These variants of the process and be effected according to known techniques.

The isomeric mixtures obtained according to the process described, mixtures, we repeat, containing predominant amount (not less than about 80%) of trans-1-(2,6,6-trimethyl-cyclohexyl)-hexan-3-ol, can be utilized directly as active perfume ingredients; their further purification is therefore superfluous in most instances. However, whenever desired, the pure trans isomer can be isolated from the said mixtures by means of preparative vapor chromatography. In practice, it has become apparent that mixtures containing proportions equal to or higher than 50% of the trans isomer together with amounts equal to or lower than 50% of the cis isomer are particularly well suited to the kinds of use considered in most areas of perfumery.

Said mixtures, or alternatively the pure trans isomer, can modify, improve or reinforce the odor properties of perfume compositions, perfume bases and concentrates as well as the scent of articles of various nature such as cosmetics, soaps, shampoos, talcs, solid and liquid detergents, households materials, e.g. waxes, space deoderants or odorants.

As will be appreciated by those skilled in the art, the amount of the composition of the invention employed in a particular instance can vary over a relatively wide range, depending upon the odorous effect to be achieved. As usual in the art, the perfumer shall determine the best concentrations as a function of the product it is desired to perfume and of the nature of the coingredients he has chosen in a particular blend. The primary requirement is to obtain a well balanced overall olfactive effect of pleasant character.

Concentrations of the order of about 1% by weight of the composition of the invention based on the total weight of the composition into which it is added, can already achieve a pronounced effect. Of course, concentrations lower than the above given value can be employed to perfume articles such as e.g. soaps, cosmetic or detergents.

The active composition of the invention can be used either in its isolated form, or, more frequently, in solution in the current solvents such as ethanol, anozol, or diethyl phthalate, or preferably in admixture with other usual perfume coingredients, supports or diluents.

The invention is illustrated in a more detailed manner by the following examples wherein the temperatures are indicated in degrees centigrade and the abbreviations have the meaning common in the art.

EXAMPLE 1

This example helps to illustrate the state of the art.

A sample of commercially available TIMBEROL [origin: Dragoco, Holzminden, FRG; for the preparation of this product, see DE-AS No. 28 07 584 and Dragoco Report, 199 (1980)] was analyzed by gas chromatography using a capillary column of 50 m length (CARBOWAX and UCON). FIG. 1 illustrates the obtained chromatogram.

The analysis of the results obtained indicated to us that the sample under examination was constituted by a mixture consisting essentially of about 64% by weight of cis-1-(2,6,6-trimethylcyclohexyl)-hexan-3-ol and about 12% of trans-1-(2,6,6-trimethylcyclohexyl)-hexan-3-ol together with other products originating, we could suppose, from the specific synthesis employed, namely 1-(2,6,6-trimethylcyclohexyl)-hexan-3-one, 2,6-dimethyl-tridecan-10-ol and 1-(2,6,6-trimethylcyclohex-1-enyl)-hexan-3-ol [see following table].

TABLE

| RT | AREA | TYPE | AR/HT | AREA % |
|---|---|---|---|---|
| 2.41 | 16439 | PV | 0.027 | 0.158 |
| 2.45 | 16178 | D VB | 0.028 | 0.156 |
| 3.91 | 15572 | PB | 0.037 | 0.150 |
| 5.38 | 18558 | BB | 0.045 | 0.098 |
| 5.65 | 18641 | VB | 0.048 | 0.182 |
| 6.17 | 14507 | PY | 0.107 | 0.148 |
| 6.99 | 28565 | PB | 0.059 | 0.275 |
| 7.25 | 49666 | PB | 0.058 | 0.478 |
| 7.44 | 161610 | BV | 0.062 | 1.555 |
| 7.54 | 247288 | VB | 0.053 | 2.379 |
| 7.81 | 7430 | PB | 0.037 | 0.072 |
| 8.06 | 21692 | BB | 0.053 | 0.209 |
| 8.27 | 21440 | BP | 0.097 | 0.206 |
| 8.59 | 4285 | PB | 0.043 | 0.041 |
| 9.00 | 43314 | PV | 0.073 | 0.417 |
| 9.12 | 55668 | VV | 0.076 | 0.536 |
| 9.46 | 757380 | VV | 0.085 | 7.285 |
| 9.59 | 615880 | VV | 0.073 | 5.924 |
| 9.66 | 697850 | VV | 0.075 | 6.713 |
| 10.04 | 6639300 | VB | 0.104 | 63.862 |
| 10.27 | 17713 | BP | 0.075 | 0.170 |
| 10.43 | 9883 | PB | 0.065 | 0.087 |
| 1071 | 894200 | BB | 0.085 | 0.601 |
| 12.39 | 11227 | BV | 0.064 | 0.108 |
| 12.51 | 15090 | VB | 0.089 | 0.145 |
| 14.58 | 14105 | BB | 0.073 | 0.136 |

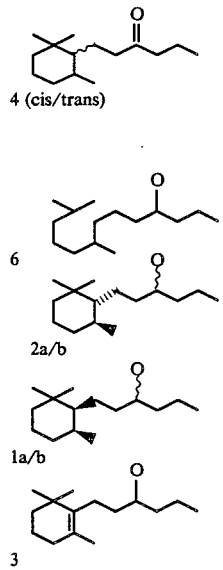

TOTAL AREA = 1.0396E+87
NUL FACTOR = 1.0000E+88

EXAMPLE 2

Preparation of
trans-1-(2,6,6-trimethylcyclohexyl)-hexan-3-ol a. 76 G (0.5M) of β-cyclocitral (commercial product; origin: BASF, Ludwigshafen, FRG) in 700 ml of cyclohexane were hydrogenated at room temperature and atmospheric pressure in the presence of 5 g of Pd at 10% on charcoal. After 8 hours and absorption of 13 l of hydrogen (0.55M), the reaction was stopped and, after filtration, the clear filtrate was evaporate and distilled by means of a Vigreux column of 10 cm length. 65 G of a colorless oil were thus obtained; B.p. 75°–6°/8.78×10² Pa (yield 84.4%), constituted by about 60% of cis-1-formyl-2,6,6-trimethylcyclohexane and 40% of its trans isomer.

b. In a three necked vessel equipped with a condenser, a thermometer, a dropping funnel and an efficient stirrer, there were placed 200 ml of anhydrous ethanol and, under nitrogen, 12.85 g (0.559 g.at.) of sodium metal.

After complete formation of the alkoxide, the reaction mixture was cooled to 20° and a mixture of 40 g (0.259M) of the product obtained according to a. above and 143.6 g (1.67M) of 2-pentanone was added therein dropwise. After having been left overnight at room temperature under stirring, the mixture was poured onto ice, acidified with 10% $H_2SO_4$ until about pH 5, and extracted with ether. The combined organic extracts were washed with brine until neutrality, dried over $Na_2SO_4$, filtered and concentrated at reduced pressure. 63.2 G of a raw material were thus obtained. By fractional distillation on a Vigreux column of 20 cm length, they gave 47.8 g of a product having B.p. 90°/1.33.Pa (yield 83.2%) consisting of about 95% by weight of trans-1-(2,6,6-trimethylcyclohexyl)-hex-1-en-3-one and about 5% of the corresponding cis isomer. A separation of a sample of this product by preparative vapor phase chromatography (CARBOWAX column of 50 m length) gave the two distinct isomers whose analytical characteristics were as follows:

trans-1-(2,6,6-trimethylcyclohexyl)-hex-1-en-3-one

IR: 3050, 1680, 1630, 1200, 1000 $cm^{-1}$;
NMR (60 MHz; $CDCl_3$): 0.71–1.118 (12H); 1.25–2.1 (10H); 2.58 (2H); 6.05 (1H); 6.48 and 6.72 (1H) δ ppm;
MS: $M^+=222$; m/e: 179(6), 161(2), 151(3), 139(10), 123(4), 109(10), 99(49, 95(19), 89(12), 69(14), 55(20), 43(100).

cis-1-(2,6,6-trimethylcyclohexyl)-hex-1-en-3-one

IR: 3050, 1680, 1630, 1200, 1000 $cm^{-1}$;
NMR (60 MHz; $CDCl_3$): 0.70–1.1 (12H); 1.25–2.1 (10H); 2.55 (2H); 6.03 (1H); 6.77 and 7.03 (1H) δ ppm.

c. 5 G of the product obtained under letter b. above were hydrogenated in the presence of 0.14 g of Raney-nickel and 0.084 g of copper chromite in an autoclave at 20 atm pressure of hydrogen and at a temperature of 140°.

The reaction was stopped after 6 hours and the mixture was filtered on diatomaceous earth. After washing the filtrate with ether and concentration at reduced pressure, there were obtained 4.71 g of a residue which by bulb distillation (150°; 13.3 Pa) gave 4.6 g of a colorless oil consisting of about 95% by weight of trans-1-(2,6,6-trimethylcyclohexyl)-hexan-3-ol and about 5% of its cis isomer (yield 90.4%). The pure isomers were separated each from the other by gas chromatography.

trans-1-(2,6,6-trimethylcyclohexyl)-hexan-3-ol

IR: 3350 $cm^{-1}$;
NMR (360 MHz; $CDCl_3$): 0.52 (1H); 0.76 (3H); 0.8–0.98 (9H); 1.35–1.65 (15H); 3.52 (1H) δ ppm;

MS: M+=226; m/e: 208(3), 193(10), 183(5), 165(5), 152(7), 138(22), 123(41), 109(54), 99(14), 95(53), 81(45), 69(89), 55(94), 43(62), 41(100).

cis-1-(2,6,6-trimethylcyclohexyl)-hexan-3-ol

IR: 3350 cm$^1$;
NMR (360 MHz; CDCl$_3$): 0,8–0,9 (6H); 0,9–0,95 (6H); 1,0–1,5 (14H); 1,9 (1H); 3,56 (1H) δ ppm;
MS: M+=226; m/e: 208(3), 193(8), 181(2), 165(2), 152(2), 138(11), 123(28), 109(33), 99(7), 95(37), 86(5), 82(40), 69(87), 55(96), 43(62), 41(100).

EXAMPLE 2A

Preparation of trans-1-(2,6,6-trimethylcyclohexyl)-hexan-3-ol

By carrying out the hydrogenation in the above described manner (see par. c.) and by using 0.180 g of wet Raney-nickel (origin: Degussa AG, FRG) and 0.140 g of copper chromite, the desired hexanol was obtained with similar yields. The observed isomeric ratio was in this case of 83% trans and 17% cis as determined by gas chromatography on OV-101 type 15 m long capillary column.

EXAMPLE 2B

Preparation of trans-1-(2,6,6-trimethylcyclohexyl)-hexan-3-ol

70 G of the product obtained under letter b. of Example 2 above were hydrogenated in the presence of 2.8 g of Raney-nickel (origin: Degussa AG, FRG) in an autoclave at 20 atm pressure of hydrogen and at a temperature of 140°.

After work-up of the reaction mixture as indicated in Example 2, 65 g of the desired hexanol were obtained (yield 92%) in an isomeric ratio of 88% trans and 12% cis as determined by gas chromatography on OV-101 type 15 m long capillary column.

EXAMPLE 3

Preparation of 1-(2,6,6-trimethylcyclohexyl)-hex-1-en-3-ol

8 G (36 mM) of the ketone, prepared according to Example 2, letter b. above, in 40 ml of ether were added dropwise in a nitrogen atmosphere to a cooled suspension at 0° of 0.42 g (11 mM) of LiAlH$_4$ in 40 ml of anhydrous ether, whereupon the temperature of the reaction mixture was slowly raised to room temperature. 0.42 Ml of water, 0.42 ml of 15% aqueous NaOH and 1.26 ml of water were successively added to the obtained mixture while a white precipitate separated. After filtration, the clear filtrate was concentrated and bulb distilled (140°; 13.3 Pa). 5.6 G (yield 70%) of the desired alcohol in an isomeric ratio of about 95% trans and 5% cis were thus obtained. The two isomers were separated each from the other by preparative gas chromatography.

trans-1-(2,6,6-trimethylcyclohexyl)-hex-1-en-3-ol

IR: 3350, 980 cm$^{-1}$;
NMR (60 MHz; CDCl$_3$): 0.6–1.1 (12H); 1.15–1.90 (12H); 4.05 (1H); 5.25–5.45 (2H) δ ppm;
MS: M+=224; m/e: 206(9), 191(6), 181(10), 163(45), 149(5), 135(11), 124(17), 109(50), 99(40), 95(43), 86(3), 81(48), 69(65), 55(55), 43(67), 41(100).

EXAMPLE 4

Preparation of 1-(2,6,6-trimethylcyclohexyl)-hexan-3-one

20 G (0.09M) of the ketone prepared according to Example 2, letter b., were hydrogenated at room temperature and atmospheric pressure in 200 ml of cyclohexane in the presence of 1.5 g of palladium at 10% over charcoal. After 2½h, 2.3 l of hydrogen were absorbed (0.09M) and the mixture was filtered. After concentration, the clear filtrate gave on distillation 20 g of the desired product having B.p. 100–110°/13.3 Pa (yield 99%).

The product obtained consisted of about 95% trans isomer and about 5% cis which isomers could be separated each from the other by gas chromatography.

trans-1-(2,6,6-trimethylcyclohexyl)-hexan-3-one

IR: 1720 cm$^{<1}$;
NMR (60 MHz; CDCl$_3$): 0.75–1.05 (12H); 1.2–2.0 (12H); 2.2–2.63 (4H)δ ppm;
MS: M+=224; m/e: 209(1), 191(4), 181(8), 163(12), 153(2), 138(20), 123(31), 109(12), 99(22), 95(28), 86(14), 82(30), 71(53), 69(53), 55(46), 43(99), 41(100).

cis-1-(2,6,6-trimethylcyclohexyl)-hexan-3-one

IR: 1720 cm$^{-1}$;
NMR (360 MHz; CDCl$_3$): 0.86 (3H); 0.88 and 0.95 (6H); 0.92 (3H); 1.03–1.65 (11H); 1.90 (1H); 2.37 (4H) δ ppm;
MS: M+=224; m/e: 204(3), 191(5), 181(8), 163(8), 150(12), 138(20), 123(29), 109(12), 99(23), 95(28), 86(21), 83(32), 69(60), 55(54), 43(100).

EXAMPLE 5

Utilization of trans-1-(2,6,6-trimethylcyclohexyl)-hexan-3-ol

A base perfume composition was prepared by mixing the following ingredients (parts by weight):

| | |
|---|---|
| Benzyl benzoate | 150 |
| Coumarin | 100 |
| Geraniol | 100 |
| Lavandin oil | 100 |
| Linalyl acetate | 100 |
| Patchouli oil | 65 |
| Phenylethanol | 75 |
| Linalol | 50 |
| Geranium oil Bourbon | 35 |
| Undecanal | 20 |
| Sandalwood oil | 20 |
| Anisic aldehyde | 5 |
| Dodecanal 50%* | 4 |
| Total | 824 |

*in diethyl phthalate

By using the above base composition, three novel compositions were prepared as follows:

| | | A | B | C |
|---|---|---|---|---|
| base composition | 8.24 | 8.24 | 8.24 | 8.24 |
| TIMBEROL | — | 1.76 | — | — |
| trans-1-(2,6,6-trimethylcyclohexyl)-hexan-3-ol[1] 5%* | — | — | 1.76 | — |
| dito pure[1] | — | — | — | 1.76 |
| | | 10 | 10 | 10 |

*in diethyl phthalate
[1] product obtained according to Example 2 (≧95% trans/≦5% cis)

Resulting compositions A, B and C were evaluated by a panel of experts who determined that the odor of composition A and B did not differ sensibly as to their strength one from the other, whereas composition C presented a powerful ambery character.

EXAMPLE 6

Utilization of trans-1-(2,6,6-trimethylcyclohexyl)-hexan-3-ol

A base perfume composition was prepared by mixing the following ingredients (parts by weight):

| Phenylethylol | 140 |
|---|---|
| Undecanal | 100 |
| Benzyl acetate | 100 |
| Hydroxycitronellal | 90 |
| Lilial ® (Givaudan) | 85 |
| Lavender oil | 85 |
| Nerol | 65 |
| Coumarin | 40 |
| Musk ketone | 40 |
| Musk ambrette | 40 |
| Linalol | 25 |
| Amyl salicylate | 20 |
| Eugenol | 20 |
| Ylang-ylang oil | 20 |
| Patchouli oil | 15 |
| Vanillin | 10 |
| Violet synth. oil | 5 |
| Total | 900 |

By using the above base composition, three novel compositions were prepared as follows:

| | A | B | C |
|---|---|---|---|
| base composition | 90 | 90 | 90 | 90 |
| TIMBEROL | — | 10 | — | — |
| trans-1-(2,6,6-trimethylcyclo-hexyl)-hexan-3-ol[1] 5%* | — | — | 10 | — |
| dito pure[1] | — | — | — | 10 |
| | 100 | 100 | 100 | 100 |

*in diethyl phthalate
[1] product obtained according to Example 2 (≧95% trans/≦5% cis)

Resulting compositions A, B and C were evaluated by a panel of experts who declared that the odor of B is analogous in strength to the odor of A. Composition C possessed a marked woody note much more pronounced than A.

What we claim is:

1. A perfume composition comprising an odorous effective amount of an odorous composition containing from 50% to 100% of trans-1-(2,6,6-trimethylcyclohexyl)hexan-3-ol- and not more than 50% of cis-1-(2,6,6-trimethylcyclohexyl)hexan-3-ol.

2. A method for improving the odor of a perfume composition which comprises adding thereto an odorous effective amount of an odorous composition containing from 50% to 100% of trans-1-(2,6,6-trimethylcyclohexyl)hexan-3-ol- and not more than 50% of cis-1-(2,6,6-trimethylcyclohexyl)hexan-3-ol.

3. A perfumed article selected from the class of soaps, cosmetics, detergents, space odorants and deodorants comprising an odorous effective amount of an odorous composition containing from 50% to 100% of trans-1-(2,6,6-trimethylcyclohexyl)hexan-3-ol and not more than 50% of cis-1-(2,6,6-trimethylcyclohexyl)hexan-3-ol.

4. A process for the preparation of essentially pure trans-1-(2,6,6-trimethylcyclohexyl)-3-hexan-3-ol which comprises the following sequentials steps:
   a. reducing β-cyclocitral through hydrogenation with a supported palladium catalyst in alcohol at about ambient temperature and at about atmospheric pressure to form 1-formyl-2,6,6-trimethylcyclohexane,
   b. adding a predetermined amount of 2-pentanone to said 1-formyl-2,6,6-trimethylcyclohexane in the presence of a strong base to form a mixture containing a predominant amount, but not less than about 95% by weight of trans-1-(2,6,6-trimethylcyclohexyl)-hex-1-en-3-one and a predetermined amount, but not more than about 5% by weight, of cis-1-(2,6,6-trimethylcyclohexyl)-hex-1-en-3one,
   c. reducing the mixture thus obtained by contacting said mixture with an alkali metal aluminohydride at a pressure between slightly above atmospheric pressure and 100 atmospheres at a temperature between about 120°-200° C. in the presence of a catalytic amount of a Raney-nickel catalyst, said catalyst optionally including a predetermined amount of copper chromite and, optionally,
   d. separating the mixture thus obtained by preparative vapor phase chromotography to form an essentially pure trans-1-(2,6,6-trimethylcyclohexyl)-hexan-3-ol.

5. The process of claim 4 wherein the addition of 2 pentanone to 1-formyl-2,6,6-trimethyl-cyclohexane is effected in the presence of at least two equivalents of an alkali metal alkoxide for one equivalent of starting material.

6. The process of claim 5 wherein the alkali metal alkoxide is sodium ethoxide.

7. A cycloaliphatic ketone of formula

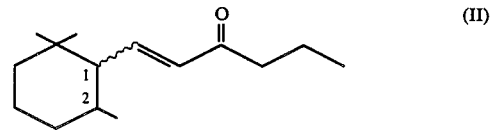

(II)

wherein the wavy line stands for a C—C bond of cis or trans configuration with respect to the methyl group in position 2 of the ring.

8. The perfume composition of claim 1 wherein the odorous composition contains more than 80% of trans-1-(2,6,6-trimethylcyclohexyl)hexan-3-ol.

9. The method of claim 2 wherein the odorous composition contains more than 80% of the trans-1-(2,6,6-trimethylcyclohexyl)hexan-3-ol.

10. The perfumed article of claim 3 wherein the odorous composition contains more than 80% of trans-1-(2,6,6-trimethylcyclohexyl)hexan-3-ol.

11. A process for the preparation of essentially pure trans-1-(2,6,6-trimethylcyclohexyl)-hexan-3-ol, which comprises the following sequential steps:
   a. adding 2-pentanone to a predetermined volume of 1-formyl-2,6,6-trimethylcyclohexane in the presence of a strong base to form a mixture containing a predetermined amount, but not less than about 95% by weight, of trans-1-(2,6,6-trimethylcyclohexyl)-hex-1-en-3-one;
   b. reducing the mixture thus obtained by contacting said mixture with an alkali metal aluminohydride at a pressure between slightly above atmospheric pressure, and 100 atmospheres at a temperature between about 120°–200° C. in the presence of a catalytic amount of a Raney-nickel catalyst, said catalyst optionally including a predetermined amount of copper chromite and, optionally, c. separating the mixture thus obtained by preparative vapor phase chromotography to form an essentially pure trans-1-(2,6,6-trimethylcyclohexyl)-hexan-3-ol.

12. The process of claim 1 wherein said reduction is carried out by contacting the β-cyclocitral with a catalyst comprising palladium over a barium carbonate support.

* * * * *